(12) United States Patent
Faulkner et al.

(10) Patent No.: US 8,784,399 B2
(45) Date of Patent: Jul. 22, 2014

(54) METHOD FOR DELIVERING INTERFERON-β

(75) Inventors: Eric Anthony Faulkner, North Andover, MA (US); Mary Diana DiBiase, Wellesley, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 112 days.

(21) Appl. No.: 11/795,092

(22) PCT Filed: Jan. 11, 2006

(86) PCT No.: PCT/US2006/001016
§ 371 (c)(1),
(2), (4) Date: Mar. 5, 2008

(87) PCT Pub. No.: WO2006/076453
PCT Pub. Date: Jul. 20, 2006

(65) Prior Publication Data
US 2008/0188823 A1 Aug. 7, 2008

Related U.S. Application Data

(60) Provisional application No. 60/643,273, filed on Jan. 12, 2005.

(51) Int. Cl.
*A61M 5/178* (2006.01)

(52) U.S. Cl.
USPC ................................................ 604/403

(58) Field of Classification Search
USPC ........................................... 604/89, 403
See application file for complete search history.

(56) References Cited

U.S. PATENT DOCUMENTS

| 4,266,557 | A | | 5/1981 | Merry |
| 4,521,237 | A | | 6/1985 | Logothetis |
| 4,647,454 | A | * | 3/1987 | Cymbalista ................... 530/351 |
| 4,895,716 | A | | 1/1990 | Goldstein et al. |
| 5,011,608 | A | * | 4/1991 | Damjanovic .................. 210/656 |
| 5,183,746 | A | | 2/1993 | Shaked et al. |
| 6,263,641 | B1 | | 7/2001 | Odell et al. |
| 6,319,225 | B1 | * | 11/2001 | Sugita et al. .................... 604/89 |
| 6,352,522 | B1 | | 3/2002 | Kim et al. |
| 6,800,735 | B2 | | 10/2004 | Whitty et al. |
| 6,906,041 | B2 | * | 6/2005 | Braun ............................ 514/44 |
| 7,029,752 | B2 | | 4/2006 | Hama et al. |
| 2003/0138910 | A1 | * | 7/2003 | Reinecke et al. ............ 435/69.1 |
| 2003/0190307 | A1 | * | 10/2003 | DiBiase et al. .............. 424/85.6 |
| 2004/0109859 | A1 | * | 6/2004 | Martin et al. ............... 424/145.1 |
| 2008/0103438 | A1 | * | 5/2008 | Prais et al. ................. 604/93.01 |

FOREIGN PATENT DOCUMENTS

| CN | 85201778 U | 4/1986 |
| CN | 2076853 U | 5/1991 |
| CN | 1245434 A | 2/2000 |
| EP | 1 258 234 | 11/2002 |
| EP | 0 948 358 | 7/2004 |

(Continued)

OTHER PUBLICATIONS

PCT International Search Report, dated Jul. 6, 2006, International Application No. PCT/US2006/001016.

*Primary Examiner* — Susan Su
(74) *Attorney, Agent, or Firm* — Steptoe & Johnson LLP

(57) ABSTRACT

The method described herein reduces the amount of aggregating metal released into solutions of Interferon-β.

39 Claims, 4 Drawing Sheets

(56) References Cited

FOREIGN PATENT DOCUMENTS

| WO | WO 98/28007 | 7/1998 |
| WO | WO-98/28007 | 7/1998 |
| WO | WO-2004/100979 | 11/2004 |
| WO | WO-2006/076453 A3 | 7/2006 |

* cited by examiner

US 8,784,399 B2

METHOD FOR DELIVERING INTERFERON-β

CROSS REFERENCE TO RELATED APPLICATIONS

This application claims priority to U.S. Ser. No. 60/643,273 filed Jan. 12, 2005. The entire contents of the aforementioned application are incorporated herein.

TECHNICAL FIELD OF THE INVENTION

This invention relates to a method for storing and delivering Interferon-β.

BACKGROUND OF THE INVENTION

Interferons are single chain polypeptides secreted by most animal cells in response to a variety of inducers, including viruses, mitogens and polynucleotides. Interferons participate in regulation of cell function, and have antiviral, antiproliferative and immunomodulating properties. Native human interferons are classified into three major types: Interferon-α (leukocyte), Interferon-β (fibroblast) and Interferon-γ (immune). Native Interferon-β is produced primarily by diploid fibroblast cells and in lesser amounts by lymphoblastoid cells.

Interferon-β is a glycoprotein. Its genetic nucleic acid and amino acid sequences have been determined. (Houghton et. al., "The Complete Amino Acid Sequence of Human Fibroblast Interferon as Deduced Using Synthetic Oligodeoxyribonucleotide Primers of Reverse Transcriptase," Nucleic Acids Research, 8, pp. 2885-94 (1980); T. Taniguchi et al., "The Nucleotide Sequence of Human Fibroblast DNA," Gene, 10, pp. 11-15 (1980)). Recombinant Interferon-β has been produced and characterized.

Interferon-β exhibits various biological and immunological activities, such as anti-viral, anti-tumor and anti-cancer. Interferon-β-1a is approved for sale in the United States for the treatment of multiple sclerosis under the trade name of Avonex®.

SUMMARY OF THE INVENTION

In general, the invention relates to a method for storing and delivering solutions of Interferon-β such that the concentration of an aggregating metal is less than 500 parts per billion in the stored solution. Aggregating metals include iron, copper, nickel, molybdenum and tungsten. Devices useful for storing Interferon-β include, but are not limited to, syringes, vials, bottles, bags and the like.

In one aspect, the invention provides a method for storing and delivering solutions of Interferon-β including providing a device having a housing for retaining the solution and filling the solution of Interferon-β into the housing. After filling the solution, the housing releases a concentration of an aggregating metal into the solution of less than 500 parts per billion.

In another aspect, the housing releases a total concentration of aggregating metals into the solution of less than 500 parts per billion, less than 250 parts per billion, less than about 100 parts per billion, less than about 75 parts per billion, less than about 50 parts per billion, or less than about than 25 parts per billion.

In still another aspect, the invention features a method for storing and delivering solutions of Interferon-β including providing a device having a housing for retaining the solution and filling the solution of Interferon-β into the housing. After filling the solution, aggregation of Interferon-β caused by aggregating metals in the solution is less than 15% after storage, less than 10% after storage, less than 5% after storage, less than 2% after storage.

In yet another aspect, the invention features a device for storing and delivering solutions of Interferon-β including a housing for retaining an Interferon-β solution and a solution of Interferon-β wherein the housing releases a total concentration of aggregating metals into the solution of less than 500 parts per billion, less than 250 parts per billion, less than about 100 parts per billion, less than about 75 parts per billion, less than about 50 parts per billion, or less than about than 25 parts per billion.

In an embodiment of this aspect, aggregation of Interferon-β caused by aggregating metals in the solution of Interferon-β contained in the housing is less than 15% after storage, less than 10% after storage, less than 5% after storage, less than 2% after storage.

Embodiments of these aspects include one or more of the following. The housing releases a concentration of an aggregating metal or total concentration of aggregating metals of less than 500 parts per billion after the solution is retained in the housing for greater than about 10 minutes, greater than about 120 minutes, greater than about 360 minutes, greater than about 480 minutes. The housing releases a concentration of an aggregating metal or total concentration of aggregating metals of less than about 500 parts per billion after the solution is retained in the housing between about 120 minutes to about 480 minutes or between about 300 minutes to about 420 minutes. The housing releases a concentration of an aggregating metal or total concentration of aggregating metals of less than about 250 parts per billion, less than about 100 parts per billion, less than about 75 parts per billion, less than about 50 parts per billion, less than about than 25 parts per billion. The aggregating metal is iron, copper, nickel, molybdenum or tungsten. The device is a syringe, bottle, vial or a bag. The housing of the device is constructed of glass, metal or plastic. The Interferon-β is Interferon-β-1a.

DETAILED DESCRIPTION OF THE INVENTION

Definitions

As used herein, the term "Interferon-β" refers to all forms of interferon-β such as interferon-β-1a.

As used herein, the term "aggregation" refers to increased interaction between Interferon molecules to cause increased opalescence, particulate formation or precipitation of the Interferon-β from solution.

As used herein, the term "aggregating metals in an amount less than a certain number of parts per billion" refers to the amount of aggregating metals which are carried from the housing of a device into a wash solution of Avonex® liquid formulation, in which the wash solution is placed in contact with the device housing for about 240 minutes to about 480 minutes, for about 300 minutes to about 420 minutes, or from about 345 minutes to about 375 minutes.

As used herein, the term "less than a certain number of parts per billion of tungsten" refers to the amount of aggregating metals which are carried from the housing of a device into a wash solution of Avonex® liquid formulation, in which the wash solution is applied to the device housing for about 240 minutes to about 480 minutes, for about 300 minutes to about 420 minutes, or from about 345 minutes to about 375 minutes.

As used herein, the term "device" refers to any means for storing or delivering Interferon-β.

As used herein, the term "housing" refers to an element of a device that is in direct contact with Interferon-β for more than about 10 minutes.

As used herein, the term "wash solution" refers to the solution, such as a placebo formulation, used to determine the amount of an aggregating metal released from the device into the solution.

As used herein, the term "placebo formulation" refers to the solution including the components of a drug composition without the drug.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In addition, the materials, methods and examples are illustrative only and not intended to be limiting.

Other features and advantages of the invention will be apparent from the following detailed description, and from the claims.

Description of the Invention

Figure 1:
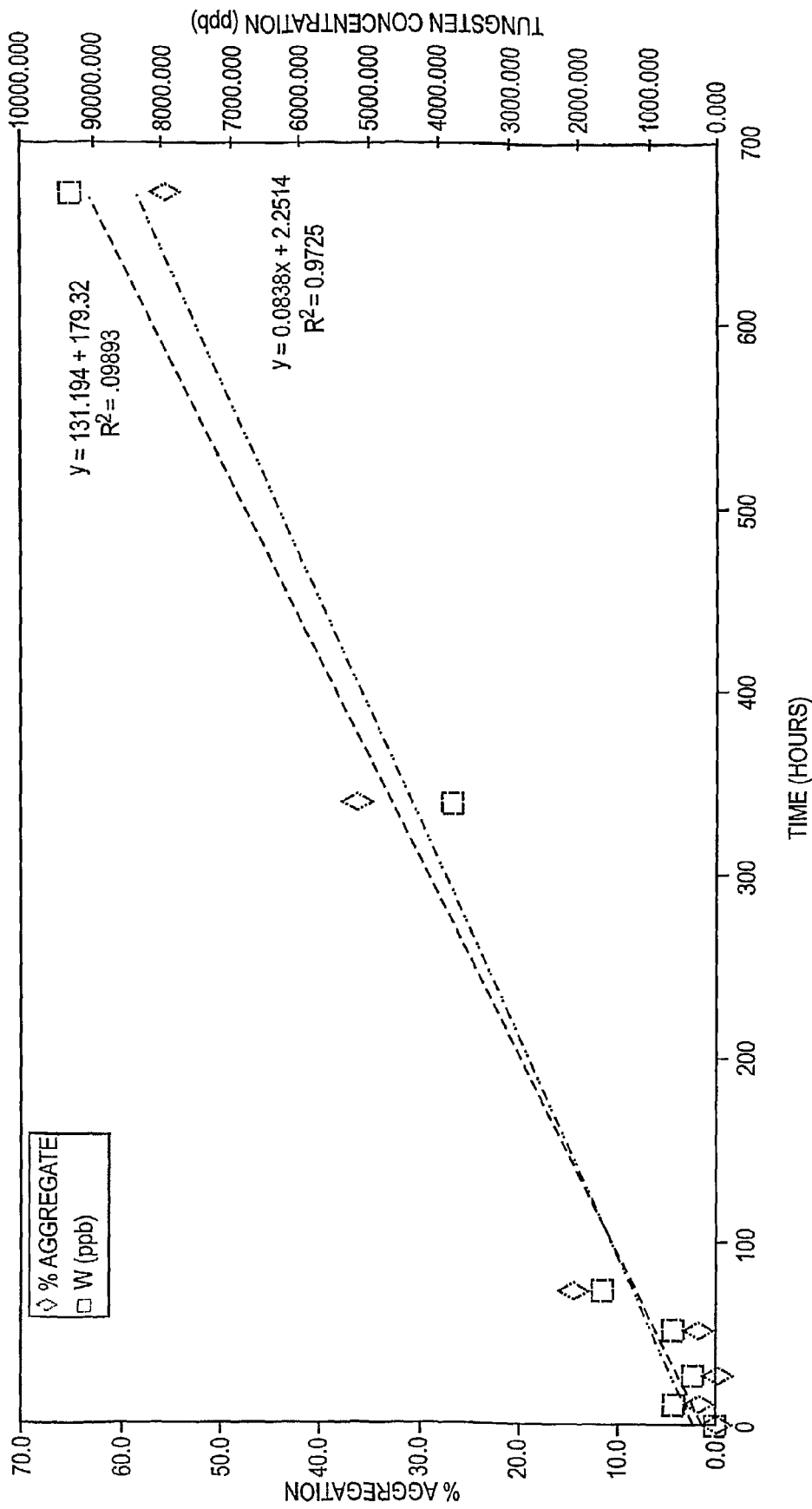
FIG. 1 is a plot of the percent aggregation of Interferon-β-1a as a function of time and the concentration of an aggregating metal, tungsten, after four weeks of storage in a commercially available syringe containing aggregating metals at 25° C. at 60% relative humidity.

In general, the invention provides a method for storing and delivering solutions of interferon-β such that the concentration of aggregating metal (each metal individually or total of all aggregating metals) is less than 500 parts per billion in the solution after storage, e.g., after storage greater than 10 minutes, 120 minutes, 360 minutes, or 480 minutes. Certain metals cause aggregation of Interferon-β. For example, as shown in FIG. 1, an increasing concentration of the aggregating metal, such as tungsten, increases the degree of aggregation of interferon-β-1a.

Aggregation is undesirable because it causes opalescence, particulate formation and precipitation of the drug. Further, aggregation can lead to a lower bioavailability of the drug and difficulty in delivering the Interferon-β. The method described herein reduces the amount of aggregating metals released into a stored solution of Interferon-β to provide less than about 15%, 10%, 5%, or 2% aggregation as measured by size exclusion chromatography.

The invention also provides a device for retaining a solution of Interferon-β so that the concentration of aggregating metals (each metal individually or the total of all aggregating metals) is less than 500 parts per billion in the solution after the solution is retained in the device for greater than 10 minutes, 120 minutes, 360 minutes, or 480 minutes. In addition, the device described herein, reduces the amount of aggregating metals released into an Interferon-β retained within the housing to provide less than about 15%, 10%, 5%, or 2% aggregation.

Figure 2:
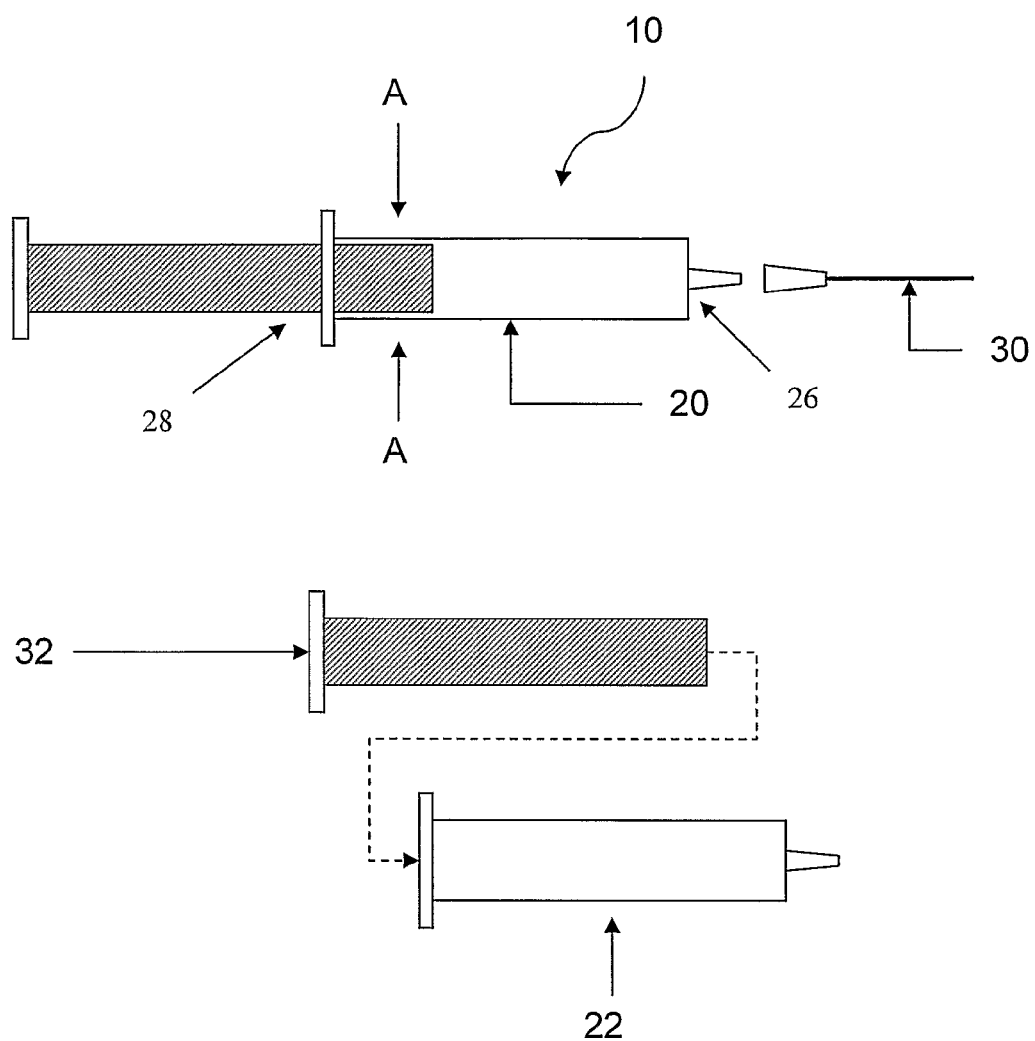
FIG. 2 illustrates a device for storing Interferon-β.
Figure 3:
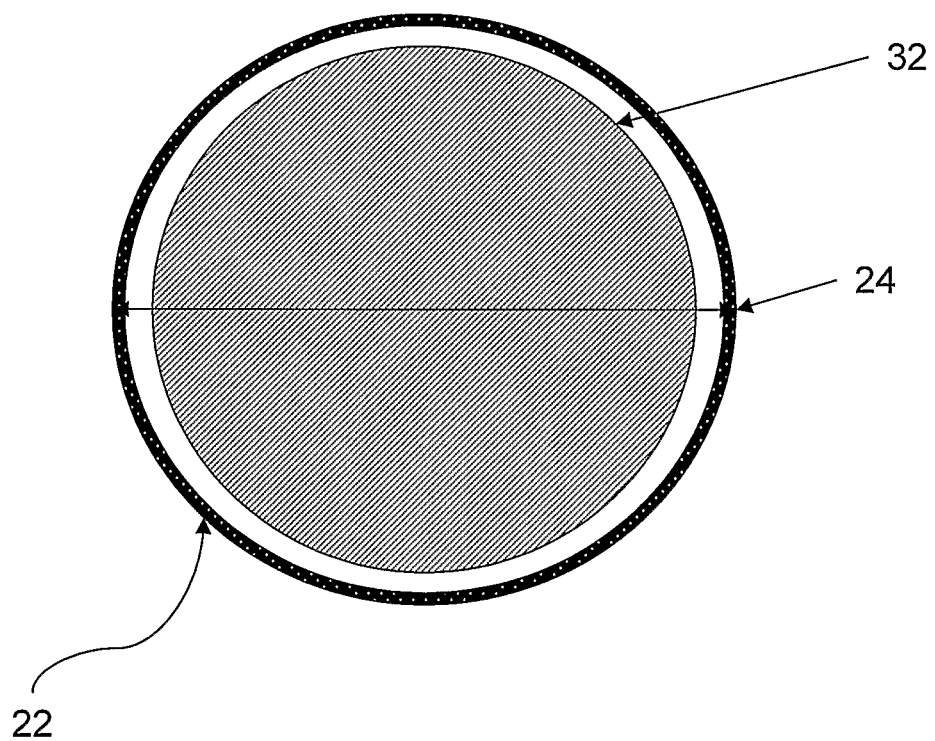
FIG. 3 is an end-on view of the device shown in FIG. 2 taken along the segment A.

Referring to FIGS. 2 and 3, a glass syringe 10 for delivering Interferon-β includes a housing 20 for holding Interferon-β-1a and a needle 30 for dispensing Interferon-β-1a from housing 20 (FIG. 2). The housing 20 includes a cylindrical wall 22 defining a central bore 24 (FIG. 3). One end 26 of the housing connects to needle 30 and the other end 28 of the housing receives a plunger 32. Plunger 32 is disposed in central bore 24 to engage frictionally cylindrical wall 22. During delivery, plunger 32 is depressed to dispense interferon-β. During storage in syringe 10, an Interferon-β solution is disposed in central bore 24 of housing 20 and is in physical contact with the end of plunger 32.

Syringe 10 is constructed or cleaned prior to use to remove or reduce the amount of aggregating metals on the surfaces of the syringe which would contact a solution of Interferon-β. Generally, syringe 10 is constructed or cleaned prior to use to remove or reduce the amount of aggregating metals, such as iron, copper, nickel, molybdenum or tungsten, released from the surfaces of the syringe that would be in contact with the Interferon-β solution during storage, e.g., greater than about 10, 120, 360, or 480 minutes, about 100, 200, 400, 700 or 1000 hours, between about 120 minutes to about 480 minutes, or between about 300 minutes to about 420 minutes of storage at temperatures between 2° C. and 30° C.

Syringe 10 is constructed or cleaned such that less than 500, 250, 100, 75, 50 or 25 parts per billion of aggregating metals (individually or in total) are released from the syringe into a solution of Interferon-β after storage. The construction or cleaning of the syringe also provides less than 15%, 10%, 5% or 2% aggregation in an Interferon-β solution after storage of the solution in the syringe. The amount of aggregating metal released into a solution of Interferon-β or placebo formulation may be measured by performing Inductively Coupled Plasma Mass Spectrometry or Atomic Absorption Spectroscopy on Interferon-β solutions or placebo formulations.

Suitable syringe storage devices capable of providing storage conditions which reduce the percent aggregation and amount of aggregating metal to levels described above are available from Becton Dickinson and Bunder Glas GmbH. Other syringe storage devices are known in the art. For example, see U.S. Pat. Nos. 6,352,522; 6,263,641; 4,895,716 and 4,266,557. These devices may be washed with concentrated sulfuric acid, e.g., 98%, to remove aggregating metals followed by one or more basic washes to neutralize any residual sulfuric acid before filling the device with Interferon-β. After washing the device with the acid and basic solutions, the amount of aggregating metal remaining in the syringe may be determined by rinsing the syringe and performing Inductively Coupled Plasma Mass Spectrometry or Atomic Absorption Spectroscopy on a placebo formulation that was stored in the syringe for more than about 10 minutes.

Figure 4:
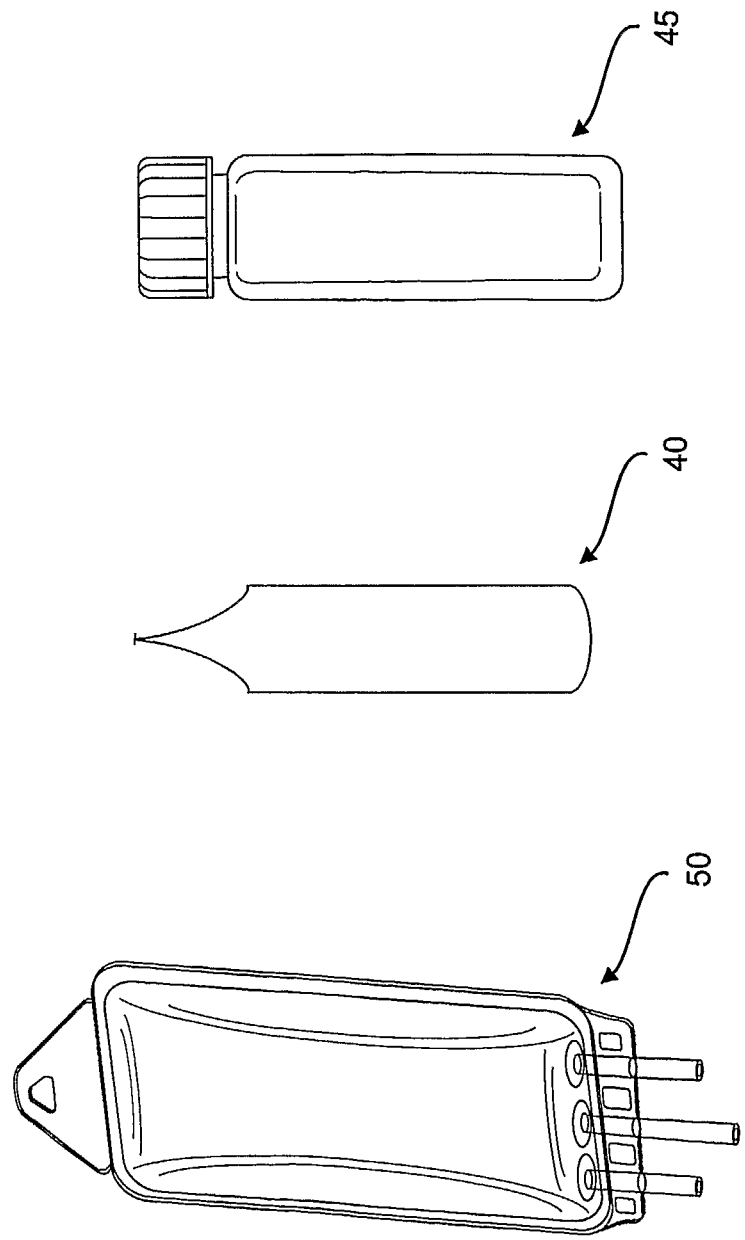
FIG. 4 illustrates alternative devices useful for storing Interferon-β.

Although the storage device is described above as a syringe, other devices for storing or delivering Interferon-β are within the scope of the invention provided that the elements of each device that are in contact with the Interferon-β for more than about 10 minutes release less than 500 parts per billion of aggregating metals into the solution of Interferon-β. Each of these devices can be manufactured to reduce the amount of aggregating metals that may release into the stored solutions or the device can be cleaned with acid and basic washes. Examples of other storage devices include ampoules (40, FIG. 4), vials (45, FIG. 4) and bags (50, FIG. 4).

The invention will be further described in the following examples, which do not limit the scope of the invention described in the claims.

EXAMPLES

Example 1

General Procedure for Determination of Aggregating Metal Release

The following procedure can be used to determine the amount of aggregating metals released into a solution after storage.

A random selection of containers in which Interferon-β is to be stored is selected from a manufacturing lot. Each container in the random selection is filled with a placebo formulation including all of the components of the formulation except Interferon-β. The filled containers are stored at ambient temperature for a period of about greater than 360 minutes. The placebo formulations are analyzed by any suitable means to determine the concentration of aggregating metals. Suitable analytical methods include, but are not limited to, Inductively Coupled Mass Spectrometry and Atomic Absorption Spectroscopy.

Example 2

Determination of Aggregating Metal Release from Avonex®

Avonex® liquid formulation contains Interferon-β-1a, sodium acetate trihydrate, glacial acetic acid, arginine hydrochloride and polysorbate-20 in Water For Injection (WFI). Specifically, each 0.5 mL (30 mcg dose) of Avonex® in a prefilled glass syringe contains 30 mcg of Interferon-β-1a, 0.79 mg sodium acetate trihydrate, 0.25 mg glacial acetic acid, 15.8 mg arginine hydrochloride and 0.025 mg polysorbate-20 in WFI at a pH of approximately 4.8. The placebo formulation is prepared by combining each of the components of the Avonex® formulation minus the Interferon-β-1a. Examples of formulations of Interferon-β are described in International Publication No. WO 98/28007 the entire contents of which are incorporated herein by reference. A random sample of syringes, such as 60, from a manufacturing lot is selected to evaluate the amount of aggregating metals released into stored solutions. The syringes are filled with the placebo formulation and stored for a period of between 360 to 480 minutes, optionally with sonication for about 5 minutes at room temperature. A sample of the placebo formulation is analyzed by Inductively Coupled Mass Spectrometry to determine the amount of aggregating metals.

Other Embodiments

It is to be understood that while the invention has been described in conjunction with the detailed description thereof, the foregoing description is intended to illustrate and not limit the scope of the invention, which is defined by the scope of the appended claims. Other aspects, advantages and modifications are within the scope of the following claims.

What is claimed is:

1. A method for storing and delivering solutions of an Interferon-β comprising:
providing a device including a housing, wherein the housing comprises an aggregating metal;
removing or reducing an amount of the aggregating metal from the device; and
filling the solution of the Interferon-β into the housing, wherein, after filling the solution, the housing releases a concentration of the aggregating metal into the solution of less than 500 parts per billion.

2. The method of claim 1, wherein the housing releases a concentration of the aggregating metal of less than 500 parts per billion after the solution is retained in the housing for greater than about 10 minutes.

3. The method of claim 2, wherein the housing releases a concentration of the aggregating metal of less than about 500 parts per billion after the solution is retained in the housing for greater than about 120 minutes.

4. The method of claim 2, wherein the housing releases a concentration of the aggregating metal of less than about 500 parts per billion after the solution is retained in the housing for greater than about 360 minutes.

5. The method of claim 2, wherein the housing releases a concentration of the aggregating metal of less than about 500 parts per billion after the solution is retained in the housing for greater than about 480 minutes.

6. The method of claim 2, wherein the housing releases a concentration of the aggregating metal of less than about 500 parts per billion after the solution is retained in the housing for about 120 minutes to about 480 minutes.

7. The method of claim 2, wherein the housing releases a concentration of the aggregating metal of less than about 500 parts per billion after the solution is retained in the housing for about 300 minutes to about 420 minutes.

8. The method of claim 1, wherein the housing releases a concentration of the aggregating metal of less than about 250 parts per billion.

9. The method of claim 1, wherein the housing releases a concentration of the aggregating metal of less than about 100 parts per billion.

10. The method of claim 1, wherein the housing releases a concentration of the aggregating metal of less than about 75 parts per billion.

11. The method of claim 1, wherein the housing releases a concentration of the aggregating metal of less than about 50 parts per billion.

12. The method of claim 1, wherein the aggregating metal is selected from the group consisting of iron, copper, nickel, molybdenum and tungsten.

13. The method of claim 12, wherein the aggregating metal is tungsten.

14. The method of claim 1, wherein the device is a syringe, bottle, vial or a bag.

15. The method of claim 14, wherein the device is a syringe.

16. The method of claim 1, wherein the housing of the device is constructed of glass, metal or plastic.

17. The method of claim 16, wherein the housing is constructed of glass.

18. The method of claim 1 further comprising cleaning the device with an acid solution.

19. The method of claim 1 further comprising constructing the device to reduce the amount of aggregating metals to less than 500 parts per billion of tungsten.

20. A method for storing and delivering solutions of an Interferon-β comprising:
providing a device including a housing, wherein the housing comprises an aggregating metal;
removing or reducing an amount of the aggregating metal from the device; and
filling the solution of the Interferon-β into the housing, wherein, after filling the solution, the housing releases a total concentration of the aggregating metal into the solution of less than 500 parts per billion.

21. The method of claim 20, wherein the housing releases a total concentration of the aggregating metal of less than about 500 parts per billion after the solution is retained in the housing for greater than about 10 minutes.

22. The method of claim 20, wherein the housing releases a total concentration of the aggregating metal of less than about 500 parts per billion after the solution is retained in the housing for greater than about 120 minutes.

23. The method of claim 20, wherein the housing releases a total concentration of the aggregating metal of less than about 500 parts per billion after the solution is retained in the housing for greater than about 360 minutes.

24. The method of claim 20, wherein the housing releases a total concentration of the aggregating metal of less than about 500 parts per billion after the solution is retained in the housing for greater than about 480 minutes.

25. The method of claim 20, wherein the housing releases a total concentration of the aggregating metal of less than about 500 parts per billion after the solution is retained in the housing for about 120 minutes to about 480 minutes.

26. The method of claim 20, wherein the housing releases a total concentration of the aggregating metal of less than about 500 parts per billion after the solution is retained in the housing for about 300 minutes to about 420 minutes.

27. The method of claim 20, wherein the housing releases a total concentration of the aggregating metal of less than about 250 parts per billion.

28. The method of claim 20, wherein the housing releases a total concentration of the aggregating metal of less than about 100 parts per billion.

29. The method of claim 20, wherein the housing releases a total concentration of the aggregating metal of less than about 75 parts per billion.

30. The method of claim 20, wherein the housing releases a total concentration of the aggregating metal of less than about 50 parts per billion.

31. The method of claim 20 further comprising cleaning the device with an acid solution.

32. The method of claim 20 comprising constructing the device to reduce the amount of aggregating metals to less than 500 parts per billion of tungsten.

33. A method for storing and delivering solutions of an Interferon-β comprising:

providing a device including a housing, wherein the housing comprises an aggregating metal;

removing or reducing an amount of the aggregating metal from the device; and filling the solution of the Interferon-β into the housing, wherein, after filling the solution, aggregation of the Interferon-β caused by the aggregating metal in the solution is less than 15% after storage.

34. The method of claim 33, wherein aggregation of Interferon-β caused by the aggregating metal in the solution is less than 10% after storage.

35. The method of claim 34, wherein aggregation of Interferon-β caused by the aggregating metal in the solution is less than 5% after storage.

36. The method of claim 33, wherein aggregation of Interferon-β caused by the aggregating metal in the solution is less than 2% after storage.

37. The method of claim 1, wherein the Interferon-β is an Interferon-β-1a.

38. The method of claim 33 further comprising cleaning the device with an acid solution.

39. The method of claim 33 comprising constructing the device to reduce the amount of aggregating metals to less than 500 parts per billion of tungsten.

* * * * *